(12) United States Patent
Hoffman

(10) Patent No.: US 6,879,657 B2
(45) Date of Patent: Apr. 12, 2005

(54) COMPUTED TOMOGRAPHY SYSTEM WITH INTEGRATED SCATTER DETECTORS

(75) Inventor: David Michael Hoffman, New Berlin, WI (US)

(73) Assignee: GE Medical Systems Global Technology, LLC, Waukesha, WI (US)

(*) Notice: Subject to any disclaimer, the term of this patent is extended or adjusted under 35 U.S.C. 154(b) by 63 days.

(21) Appl. No.: 10/063,752

(22) Filed: May 10, 2002

(65) Prior Publication Data

US 2003/0210761 A1 Nov. 13, 2003

(51) Int. Cl.[7] .................................................. G01N 23/00
(52) U.S. Cl. .............................. 378/7; 378/19; 378/87; 378/88; 378/90
(58) Field of Search .............................. 378/7, 19, 57, 378/86, 87, 88, 89, 90

(56) References Cited

U.S. PATENT DOCUMENTS

| | | | | |
|---|---|---|---|---|
| 4,670,894 A | * | 6/1987 | Birnbach et al. | 378/122 |
| 4,799,247 A | * | 1/1989 | Annis et al. | 378/87 |
| 4,995,107 A | * | 2/1991 | Klingenbeck | 378/7 |
| 5,025,463 A | * | 6/1991 | Saito et al. | 378/19 |
| 5,181,234 A | * | 1/1993 | Smith | 378/87 |
| 5,260,982 A | * | 11/1993 | Fujii et al. | 378/87 |
| 5,684,855 A | * | 11/1997 | Aradate et al. | 378/4 |
| 5,696,806 A | * | 12/1997 | Grodzins et al. | 378/86 |
| 5,930,326 A | * | 7/1999 | Rothschild et al. | 378/57 |
| 6,094,472 A | * | 7/2000 | Smith | 378/86 |
| 6,175,609 B1 | | 1/2001 | Edic et al. | |
| 6,470,067 B1 | * | 10/2002 | Harding | 378/19 |
| 6,553,096 B1 | * | 4/2003 | Zhou et al. | 378/122 |
| 6,556,653 B2 | * | 4/2003 | Hussein | 378/90 |
| 6,661,867 B2 | * | 12/2003 | Mario et al. | 378/57 |
| 6,744,845 B2 | * | 6/2004 | Harding et al. | 378/16 |

* cited by examiner

Primary Examiner—Allen C. Ho
(74) Attorney, Agent, or Firm—Artz & Artz, PC

(57) ABSTRACT

An imaging system includes an x-ray source coupled to a gantry. The x-ray source generates an x-ray flux, wherein a portion of the x-ray flux becomes scatter radiation. A scatter detector is also coupled to the gantry to receive the scatter radiation. The scatter detector generates a scatter signal in response to the scatter radiation, and a host computer receives the scatter signal.

16 Claims, 3 Drawing Sheets

COMPUTED TOMOGRAPHY SYSTEM WITH INTEGRATED SCATTER DETECTORS

BACKGROUND OF INVENTION

The present invention relates generally to imaging systems and more particularly to computed tomography. A computed tomography or CT scan is a method of taking pictures of the inside of the body using an ultra-thin x-ray beam. As the x-ray beam passes through the body, it is absorbed by bones, tissues and fluid within the body, thereby varying resultant beam intensity. The intensity of the x-ray beam emerging from the body is measured by a device that converts x-ray beam data into a detailed picture.

Multi-slice CT scanners are special CT systems equipped with a multiple-row detector array rather than a single-row detector array. This allows for simultaneous scan of multiple slices at different locations.

A typical CT scanner includes a gantry having an annular frame for rotatably supporting an annular disk about a rotation or scanning axis of the scanner. The disk includes a central opening large enough to receive a patient extending along the scanning axis, and the disk is rotated about the patient during a scanning procedure. An x-ray tube is positioned on the disk diametrically across the central opening from an array of x-ray detectors. As the disk is rotated, the x-ray tube projects a beam of energy, or x-rays, along a scan plane, through the patient, and to the detector array. By rotating the x-ray source about the scanning axis and relative to the patient, x-rays are projected through the patient from many different directions. An image of the scanned portion of the patient is then constructed from data provided by the detector array using a scanner computer.

A disadvantage of the aforementioned system is that acquiring further information requires either an increased dose of x-rays or an increased number of x-ray scans.

A further disadvantage of the aforementioned system is that back-scatter radiation is not utilized to obtain an increase amount of information about the patient. Back-scattering is the deflection of radiation or particles by scattering through angles greater than 90° with reference to the original direction of travel.

The disadvantages associated with current, CT systems have made it apparent that a new technique for CT scanning and data transfer is needed. The new technique should substantially increase information acquired from each patient and should also utilize back-scatter x-rays as a source of information. The present invention is directed to these ends.

SUMMARY OF INVENTION

In accordance with one aspect of the present invention, an imaging system includes a gantry and an x-ray source coupled to the gantry. The x-ray source is adapted to generate an x-ray flux, wherein a portion of the x-ray flux is adapted to become scatter radiation. A first scatter detector is also coupled to the gantry and is adapted to receive the scatter radiation. The scatter detector is further adapted to generate a first scatter signal in response to the scatter radiation. A host computer is adapted to receive the scatter signal.

In accordance with another aspect of the present invention, a method for data collection for an imaging system comprising: activating an x-ray source; generating an x-ray flux; receiving scatter radiation from said x-ray flux in at least one scatter detector; generating a scatter signal in response to said x-ray flux; and receiving said scatter signal in a host computer.

One advantage of the present invention is that it generates an increased amount of information from a scanned object without the need for increased dosage or an increased number of scans.

Additional advantages and features of the present invention will become apparent from the description that follows and may be realized by the instrumentalities and combinations particularly pointed out in the appended claims, taken in conjunction with the accompanying drawings.

BRIEF DESCRIPTION OF DRAWINGS

For a more complete understanding of the invention, there will now be described some embodiments thereof, given by way of example, reference being made to the accompanying drawings, in which.

DETAILED DESCRIPTION

The present invention is illustrated with respect to a Computed Tomography (CT) scanning system 10, particularly suited to the medical field. The present invention is, however, applicable to various other uses that may require CT scanning, as will be understood by one skilled in the art.

Figure 1:
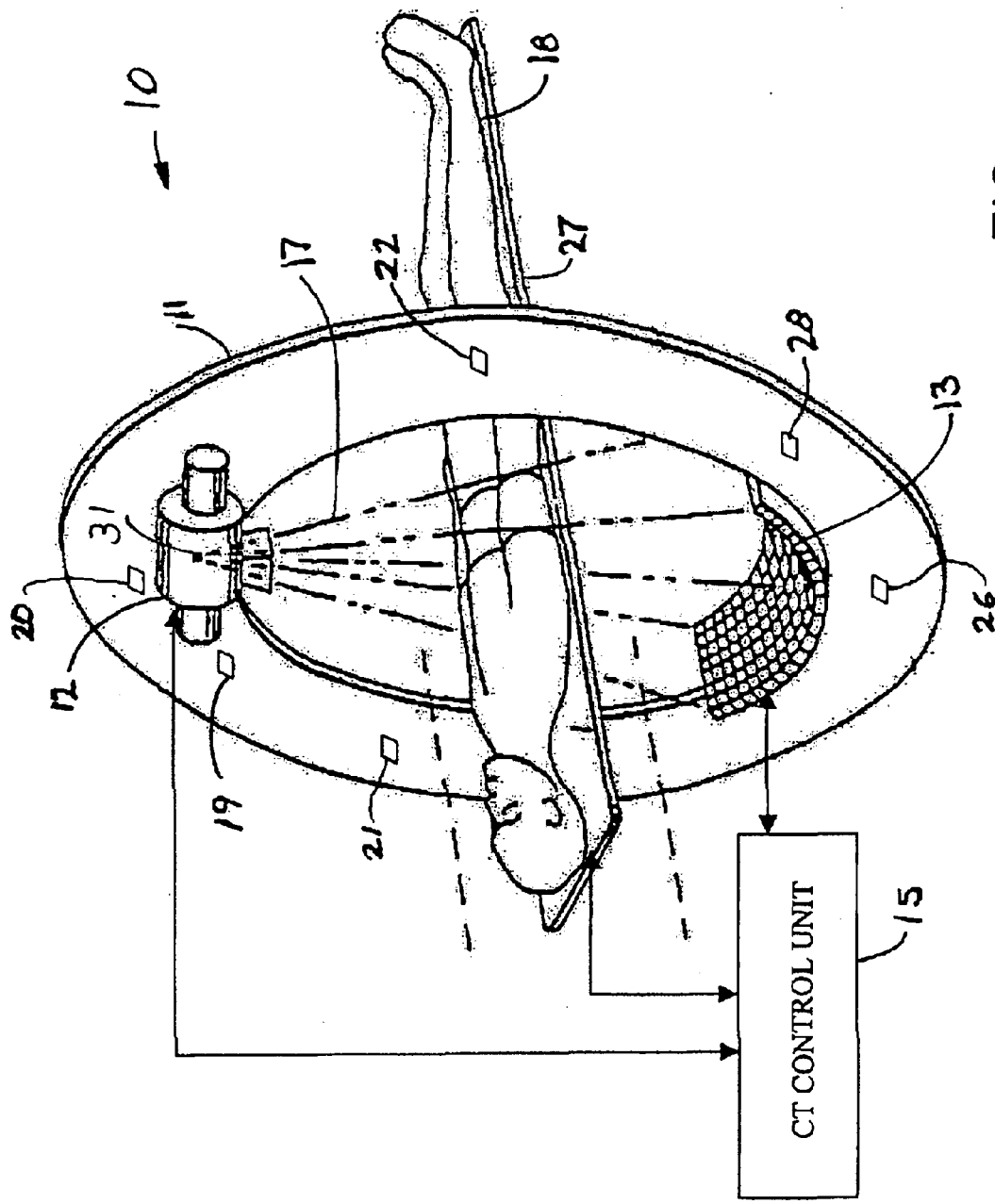
FIG. 1 is a diagram of a CT scanning system in accordance with a preferred embodiment of the present invention.
Figure 2:
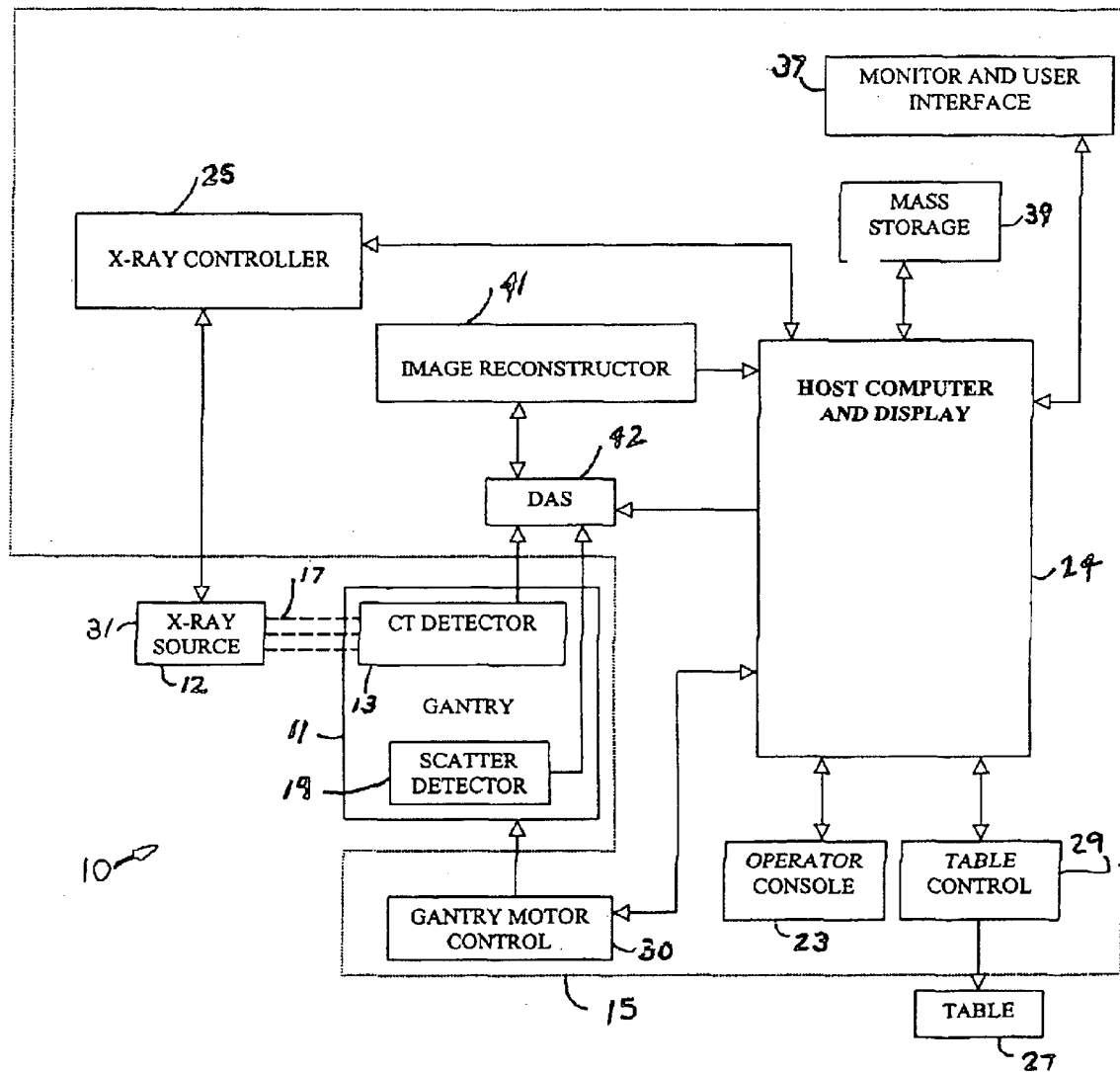
FIG. 2 is a block diagram of FIG. 1.

Referring to FIGS. 1 and 2, a CT scanning system 10 including a gantry 11, in accordance with a preferred embodiment of the present invention, is illustrated. An x-ray source 12, coupled to the gantry 11, generates an x-ray flux 17, which passes through an object 18 (e.g. a patient) and produces back-scatter radiation. The system 10 further includes a CT detector 13, coupled to the gantry 11, which generates a detector signal in response to the x-ray flux 17. A first scatter detector 19, generating a scatter signal in response to the scatter radiation, is also coupled to the gantry 11. Position and operation of the scatter detector 19 will be discussed later.

A CT control unit 15, including a host computer and display 24 and various other widely known CT control and display components, receives the detector and scatter signals and responds by generating an image signal. The CT control unit 15 also includes, for example, an operator console 23, an x-ray controller 25, a table control 29, a gantry motor control 30, a mass storage 39, an image reconstructor 41 and a data acquisition system 42, all of which will be discussed later.

The gantry 11 is the ring shaped platform that rotates around the scanned object 18 in response to signals from the gantry motor control 30, as will be understood by one skilled in the art. Ideally, the x-ray source 12, CT (multi-slice) detector 13 and scatter detector 19 are coupled thereto.

The x-ray source 12 is embodied as a flat panel x-ray source or an extended x-ray source 31 (e.g. Imatron), or a standard x-ray tube. The x-ray source 12 is activated by either a host computer 24 or an x-ray controller 25, as will be understood by one skilled in the art. The x-ray source 12 sends the x-ray flux 17 through an object 18 on a moveable table 27 controlled by a table control device 29 acting in response to signals from the host computer 24, as will be understood by one skilled in the art.

The x-ray flux 17 from the x-ray source 12 passes through the patient and impinges on the x-ray detector 13. The signal 17 passes directly to the host computer and display 24, where the signal is converted to a gray level corresponding to the attenuation of the x-ray photon through the patient, for the final CT image.

The CT detector 13 is typically located opposite the x-ray source 12 to receive x-ray flux 17 generated therefrom and includes several modules. Each module shares information with other modules corresponding to a number of slices.

Modern CT detectors typically have N slices in the table motion direction, where N is 4,8,16, or other number depending on system requirements. These multi-slice configurations extend area of coverage and offer reduced scan times and increased resolution.

The first scatter detector 19 is coupled to the gantry 11 however, numerous additional scatter detectors 20, 21, 22, 26, and 28, are coupled thereto to receive increased levels of back-scatter radiation. These scatter detectors can be from single cell to multiple cell detectors utilizing single slice or multiple slice configurations. They can also be a complete duplicate of detector 13 placed at these designated locations. Examples of locations on the gantry 11 for a first and a second scatter detector 19, 20 is on either side of the x-ray tube 12 (on a first side and a second side of the x-ray tube), the pair of scatter detectors 21, 22 on the other two sides of the X-ray tube 12 a portion of the circumference around the gantry 11 or alternately the pair of scatter detectors 26, 28 on both or on only one side of the CT detector 13.

The scatter detector 19 is ideally coupled relatively close to the x-ray source 12 and measures back-scattered x-ray flux as a function of the rotation angle of the gantry 11. The detected scatter radiation versus view angle is utilized similarly to that of the transmitted x-ray flux to generate a CT image. The image is generated either during a standard CT scan or during a separate scan with alternate optimized x-ray radiation.

The present invention is illustrated with respect to CT, however it is alternately used for any type of x-ray system using detectors including mammography, vascular x-ray imaging, bone scanning, etc. Further embodiments include non-medical applications such as weld inspection, metal inspection. Essentially, anything that could use a digital x-ray detector to make 1, 2 or 3 dimensional images.

The host computer 24 receives the detector signal and the first scatter signal. The host computer 24 also activates the x-ray source 12, however, alternate embodiments include independent activation means for the x-ray source. The present invention includes an operator console 23 for control by technicians, as will be understood by one skilled in the art.

Data is acquired and processed, and a CT image, for example, is presented to a radiology technician through the monitor and user interface 37 while the scan is occurring. The host computer 24 needs only read the module and scatter signals and update the display at the appropriate locations through, for example, an image reconstructor 41 and data acquisition system (DAS) 42. The host computer 24 alternately stores image data in a mass storage unit 39 for future reference.

An alternate embodiment incorporates a similar host computer 24 in a flat panel x-ray source, such as the GE Senographe 2000D Full Field Digital Mammography System.

One embodiment of the present invention incorporates use of x-ray detectors for the scout scan on a CT system. During a scout scan from the x-ray source to the detector elements, the x-ray tube remains stationary while the patient table 27 translates under the x-ray flux 17. This results in a two-dimensional image ideal for qualitative information and for locating the desired position for scanning during further CT exams.

Figure 3:
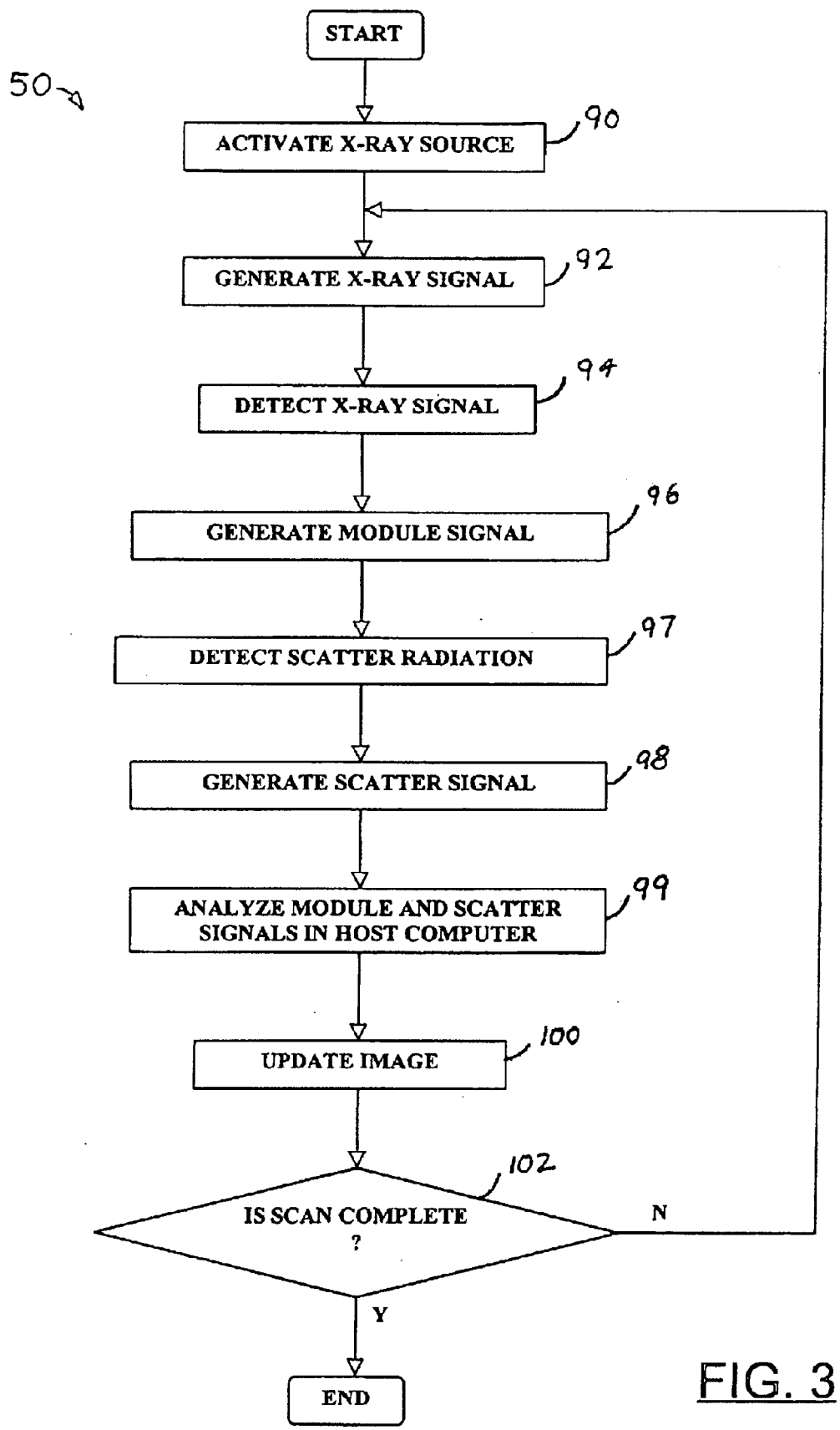
FIG. 3 is a block diagram of a method for scanning an object, in accordance with a preferred embodiment of the present invention.

Referring to FIG. 3, a block diagram of a Computed Tomography (CT) scanning system 50 is illustrated. Logic starts in operation block 90 where the x-ray source is activated by the host computer. Subsequently, in operation block 92, the x-ray source generates an x-ray flux (signal), which typically travels through a patient.

Operation block 94 then activates, and the CT detector detects the x-ray flux and generates at least one detector signal, in operation block 96, in response to the x-ray flux.

Operation block 97 then activates, and the scatter detector detects the scatter radiation and generates at least one scatter signal, in operation block 98, in response to the scatter radiation resulting from the x-ray signal.

Operation block 99 then activates, and the host computer analyzes the detector signals, and updates the resultant scan image in operation block 100.

A check is then made in inquiry block 102 whether the scan is complete. For a positive response, the host computer stops scanning. Otherwise, operation block 92 reactivates and blocks 94, 96, 97, 98, 99, 100 and 102 subsequently activate in turn.

In operation, the method for data collection for an imaging system includes the steps of activating an x-ray source, thereby generating an x-ray flux. Following reception of the x-ray flux in at least one CT detector, a detector signal is generated and subsequently received in a host computer. Scatter radiation from the x-ray flux is received in at least one scatter detector, which generates a signal therefrom, which is received in the host computer.

The host computer cycles typical image processing steps in response to the detector and scatter signals, as will be understood by one skilled in the art. In other words, data offsets are corrected and x-ray dosage is measured and normalized. Necessary calibration corrections are made, and the resulting signal is filtered, typically through a low dose filter and an adaptive filter, to reduce noise in the signal. The signal is then converted to display pixel format and subsequently displayed.

From the foregoing, it can be seen that there has been brought to the art a new computed tomography scanning system 10. It is to be understood that the preceding description of the preferred embodiment is merely illustrative of some of the many specific embodiments that represent applications of the principles of the present invention. Numerous and other arrangements would be evident to those skilled in the art without departing from the scope of the invention as defined by the following claims.

What is claimed is:

1. An imaging system comprising:
    a gantry;
    an x-ray source coupled to said gantry, said x-ray source generating an x-ray flux, wherein a portion of said x-ray flux becomes scatter radiation;
    a first scatter detector coupled to said gantry, said first scatter detector receiving said scatter radiation, said first scatter detector further generating a first scatter signal in response to said scatter radiation;

a host computer receiving said first scatter signal and generating therefrom an image; and a CT detector coupled to said gantry, said CT detector adapted to generate a detector signal in response to said x-ray flux.

2. The system of claim 1, wherein said first scatter detector is positioned substantially adjacent to said CT detector.

3. The system of claim 1, wherein said first scatter detector is positioned substantially adjacent to said x-ray source.

4. The system of claim 1, further comprising a second scatter detector coupled to said gantry.

5. The system of claim 4, wherein said first scatter detector is positioned on a first side of said CT detector and said second scatter detector is positioned on a second side of said CT detector.

6. The system of claim 4, wherein said first scatter detector and said second scatter detector are positioned on only one side of said CT detector.

7. The system of claim 1, wherein said x-ray source comprises an extended x-ray source.

8. A method for data collection for an imaging system comprising:

activating an x-ray source;

generating an x-ray flux;

receiving scatter radiation from said x-ray flux in at least one scatter detector coupled to a rotating gantry;

generating a scatter signal in response to said x-ray flux;

receiving said scatter signal in a host computer; and generating an image from said scatter signal.

9. The method of claim 8, further comprising generating a two dimensional image.

10. A computed tomography system comprising:

a gantry;

an x-ray source coupled to said gantry, said x-ray source generating an x-ray flux;

a CT detector coupled to said gantry, said CT detector generating a detector signal in response to said x-ray flux;

a first scatter detector coupled to said gantry, said first scatter detector generating a first scatter signal in response to said x-ray flux; and a host computer receiving said detector signal and said first scatter signal and generating an image from said first scatter signal.

11. The system of claim 10, wherein said x-ray source comprises an extended area x-ray source.

12. The system of claim 10, wherein said first scatter detector is positioned substantially adjacent to said CT detector.

13. The system of claim 10, wherein said first scatter detector is positioned adjacent to said x-ray source.

14. The system of claim 10, further comprising a second scatter detector coupled to said gantry.

15. The system of claim 14, wherein said first scatter detector is positioned on a first side of said CT detector and said second scatter detector is positioned on a second side of said CT detector.

16. The system of claim 14, wherein said first scatter detector and said second scatter detector are positioned on only one side of said CT detector.

* * * * *